United States Patent [19]
Dugan

[11] Patent Number: 5,942,247
[45] Date of Patent: *Aug. 24, 1999

[54] METHOD FOR TREATING PEDIATRIC HIGH GRADE ASTROCYTOMA INCLUDING BRAIN STEM GLIOMA

[75] Inventor: Margaret H. Dugan, Woodside, N.Y.

[73] Assignee: Schering Corporation, Kenilworth, N.J.

[*] Notice: This patent is subject to a terminal disclaimer.

[21] Appl. No.: 08/902,381

[22] Filed: Jul. 29, 1997

Related U.S. Application Data

[60] Provisional application No. 60/022,829, Jul. 31, 1996.

[51] Int. Cl.$^6$ ..................................................... A61K 31/33
[52] U.S. Cl. ............................................ 424/451; 514/183
[58] Field of Search .............................. 424/451; 514/183

[56] References Cited

U.S. PATENT DOCUMENTS 5,731,304  3/1998  Baer et al. .

FOREIGN PATENT DOCUMENTS

94/15615  7/1994  WIPO .

OTHER PUBLICATIONS

Newlands, *British J. Cancer*, 65(2), 287–292 (1992).
Bleehen et al, *J. Clinical Oncology*, 13(4), 910–913 (1994).
O'Reilly et al, *European J. cancer*, 29A, 940 (1993).
Stevens et al, *J. Medicinal Chem.*, 27, 196–201 (1984).
Wang et al, *J. Chem. Soc.–Chem. Comm.*, 1687–1688 (1994).
Newlands et al, The Charing Cross Hospital Experience with Temozolomide in Patients with Gliomas, European Journal of Cancer, vol. 32A, No. 13, pp. 2236–2241, Dec. 1996.

*Primary Examiner*—Thurman K. Page
*Assistant Examiner*—Brian K. Seidleck
*Attorney, Agent, or Firm*—Palaiyur S. Kalyanaraman

[57] ABSTRACT

There is disclosed a method for treating high grade astrocytoma, especially brain stem glioma, in a child by administering to a child in need of such treating an amount of temozolomide sufficient to achieve a clinical response. Preferred dosing schedules are provided.

16 Claims, No Drawings

METHOD FOR TREATING PEDIATRIC HIGH GRADE ASTROCYTOMA INCLUDING BRAIN STEM GLIOMA

This application claims the benefit of U.S. Provisional Application No. 60/022,829, filed Jul. 31, 1996.

This invention relates to the treatment of certain cancers in children and in particular to the treatment of cancers in children with temozolomide Temozolomide is known for its anti-tumor effects. For example, in one study clinical responses were achieved in 17% of patients having advanced melanoma (Newlands ES, et al. Br J Cancer 65 (2) 287–2981, 1992). In another study a clinical response was achieved in 21% of patients with advanced melanoma (Journal of Clinical Oncology, Vol 13, No. 4 (April), 1995, pp 910–913). Treatment of high grade glioma in adults with temozolomide is also known, Eur. J. Cancer 1993; 29A:940. However treating cancers in children with temozolomide is not well known. This invention is predicated on the discovery that temozolomide is effective in treating a very difficult type of cancer in children—high grade astrocytoma, including brain stem glioma.

SUMMARY OF THE INVENTION

This invention may be summarized as a method for treating high grade astrocytoma, including brain stem glioma, in a child in need of such treating comprising administering temozolomide in an amount sufficient to achieve a clinical response. Preferred dosing schedules are listed below.

As used herein the term children and child is intended to mean a human being of age 18 years or less. As used herein the term patient or patients is intended to mean a child or children.

DETAILED DESCRIPTION

All references cited herein are incorporated herein by reference.

The term "temozolomide" is intended to mean a compound having the formula:

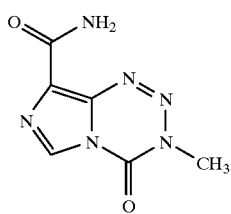

One chemical name for temozolomide is 3,4-dihydro-3-methyl-4-oxoimidazo-[5,1-d]1,2,3,4-tetrazin-8-carboximide. The synthesis of temozolomide is well known. See, for example, Stevens et al., J. Med. Chem, 1984, 27, 196–201 and Wang et al., J. Chem. Soc., Chem. Commun., 1994, pp 1687–1688.

The pediatric cancer treatable by this invention is high grade astrocytoma, including brain stem glioma. This invention contemplates treating this cancers at any stage from the discovery of the cancer to the advanced stage.

A child suffering from high grade astrocytoma may exhibit one or more of the following signs or symptoms:

(a) presence of cancerous tumor in the brain or brainstem.

(b) fatigue, (c) pain, (d) decreased performance status from tumor burden, and (e) other well known symptoms associated high grade astrocytoma including brainstem glioma.

To practice the invention, temozolomide is administered to the patient exhibiting one of more of the above signs or symptoms in an amount sufficient to eliminate or at least alleviate one or more of the signs or symptoms.

The preferred dosage of temozolomide for practicing this invention is a total dose of 500 to 1200 mg/m$^2$ of the patient's body surface area, administered over a period of from 2 to 28 consecutive days, more preferable over a period of from 4 to 7 consecutive days, and most preferably over a period 5 consecutive days. Thus if the total dose is to be 1000 mg/m$^2$ administered over a period of 5 days, the daily dose for this period would be 200 mg/m$^2$. The daily doses may be administered once per day after four hours of fasting, followed by two hours of fasting, which is conventional for temozolomide. Alternatively the temozolomide may be administered more than once per day as disclosed in our co-pending U.S. patent application Ser. No. 08/902,380 (presently identified as attorney's docket no. OC626) filed of even date herewith.

After a period of about 28 to 42 days, more preferably 28 to 35 days, and most preferably 28 days, from the first day of temozolomide administration, another administration cycle may be performed, with temozolomide being re-administered on day one and on each subsequent day of the administration period.

As another administration method, the temozolomide may be administered for a much longer period at reduced dosage. For example, the temozolomide could be administered daily for up to 6 or 7 weeks at a dosage of 50 to 100 mg/m$^2$/day, more preferably 75 mg/m$^2$.

Temozolomide may be administered orally in capsule form wherein it is admixed with conventional pharmaceutical carriers. Preferred temozolomide capsule formulations are:

| Ingredient | mg/Capsule | | | |
|---|---|---|---|---|
| temozolomide | 5 | 20 | 100 | 250 |
| Anhydrous Lactose NF | 132.8 | 182.2 | 175.7 | 154.3 |
| Sodium Starch Glycolate NF | 7.5 | 11.0 | 15.0 | 22.5 |
| Colloidal Silicon Diozide NF | 0.2 | 0.2 | 0.3 | 0.7 |
| Tartaric Acid NF | 1.5 | 2.2 | 3.0 | 9.0 |
| Steric Acid NF | 3.0 | 4.4 | 6.0 | 13.5 |
| Capsule Size* | 3 | 2 | 1 | 0 |

*White opaque, preservative-free, two-piece hard gelatin capsules

The treatment cycles may be continued until disease progression or intolerable side effects are encountered. The dosage may be decreased, if intolerable side effects or hemotologic toxicity are encountered.

A common, but tolerable side effect of temozolomide is nausea and vomiting. This can be alleviated by administering an anti-emetic in conjunction with the temozolomide. It is preferred that the anti-emetic Ondansetron be given p.o. in a dose of about 8 mg about 30 minutes before temozolomide administration. Of course other anti-emetics such as Hasaldol, Benadryl, and Ativan may also be used as needed.

Of course, other forms of administration of temozolomide, as they become available, are contemplated, such as by IV injection or infusion, intrathecally, by sustained release dosage form, syrup, suppository, transdermal, nasal spray, etc.. Any form of administration will work so long as the proper dosage is delivered without destroying the temozolomide.

The effectiveness of treatment may be determined by controlled clinical trials. Patients having a cancer treatable by this invention with measurable or evaluable tumors will be included in the study. A measurable tumor is one that can be measured in at least two dimensions. An evaluable tumor is one that can be measured in one dimension.

The tumor will be measured or evaluated before and after treatment by whatever means provides the most accurate measurement, such as CT scan, MRI scan, etc. New tumors or the lack thereof in previously irradiated fields can also be used to assess the anti-tumor response. The criteria for evaluating response will be similar to that of the WHO Handbook of Reporting Results of Cancer Treatment, WHO Offset Publication 1979, 49-World Health Organization, Geneva. The following results are defined for uni- and bi-dimensionally measurable tumors.

Complete response: Complete disappearance of all clinically detectable malignant disease determined by two observations not less than four weeks apart.

Partial Response: (a) for bidimensionally measurable tumors, a decrease of at least 50% in the sum of the products of the largest perpendicular diameters of all measurable tumors as determined by two observations not less than four weeks apart. (b) for unidimensionally measurable tumors, a decrease by at least 50% in the sum of the largest diameters of all tumors as determined by two observations not less than four weeks apart. In cases where the patient has multiple tumors, It is not necessary for all tumors to have regressed to achieve a partial response as defined herein, but no tumor should have progressed and no new tumor should appear.

Stable disease: (a) for bidimensionally measurable tumors, less than a 50% decrease to less than a 25% increase in the sum of the products of the largest perpendicular diameters of all measurable tumors. (b) for unidimensionally measurable tumors, less than a 50% decrease to less than a 25% increase in the sum of the diameters of all tumors. For (a) and (b) no new tumors should appear.

Progressive disease is defined as an increase of 25% or greater in the product of the largest perpendicular diameters for at least one bidimensionally measurable tumor, or an increase of 25% or greater at least one unidimensionally measurable tumor, or appearance of a new lesion.

For patients having both uni- and bi-dimensionally measurable tumors, the overall response will be determined in accordance with the following table.

| Response in bidimensionally measurable disease | Response in unidimensionally measurable disease | Overall Response |
| --- | --- | --- |
| PD | any | PD |
| Any | PD | PD |
| SD | SD or PR | SD |
| SD | CR | PR |
| PR | SD or PR or CR | PR |
| CR | SD or PR | PR |
| CR | CR | CR |

Abbreviations: PD: Progressive Disease CR: Complete Response PR: Partial Response SD: Stable Disease Of course elimination or alleviation of other known signs or symptoms of high grade astrocytoma, especially those listed previously, can also be used to evaluate the effectiveness of this invention.

The cancers should be evaluated, i.e. tumors measured, etc., no more than 14 days before the start of the treatment. These cancers should be reevaluated about 28 days after day 1 of administration of the first dose of temozolomide. Twenty eight days after this initial administration another administration and evaluation may be performed. The treatment cycles and evaluations may be continued until disease progression or unacceptable toxicity is encountered.

I claim:

1. A method for treating high grade astrocytoma in a child in need of such treating said method consisting of administering temozolomide and an antiemetic to said child, wherein the temozolomide is present in 500–1,200 mg per $m^2$ based on the child's body surface area and the antiemetic is administered orally in an amount of about 8 mg about 30 minutes prior to administering said temozolomide.

2. The method of claim 1 wherein the temozolomide and antiemetic are administered over a period of from 2 to 28 days.

3. The method of claim 1 wherein the temozolomide and antiemetic are administered over a period of from 4 to 7 days.

4. The method of claim 1 wherein the temozolomide and antiemetic are administered over a period of 5 days.

5. The method of claim 2 wherein after a period of 28 to 42 days after the first day of the temozolomide and antiemetic administration period, the temozolomide and antiemetic administrations are repeated.

6. The method of claim 4 wherein after a period of 28 days after the first day of the temozolomide and antiemetic administration period, the temozolomide and antiemetic administrations are repeated.

7. The method of claim 1 wherein the temozolomide is administered daily for at least 6 weeks at a dosage of 50 to 100 $mg/m^2/day$.

8. The method of claim 7 wherein the dosage of temozolomide is 75 $mg/m^2/day$.

9. The method of claim 1 wherein the high grade astrocytoma is brain stem glioma.

10. The method of claim 2 wherein the high grade astrocytoma is brain stem glioma.

11. The method of claim 3 wherein the high grade astrocytoma is brain stem glioma.

12. The method of claim 4 wherein the high grade astrocytoma is brain stem glioma.

13. The method of claim 5 wherein the high grade astrocytoma is brain stem glioma.

14. The method of claim 6 wherein the high grade astrocytoma is brain stem glioma.

15. The method of claim 7 wherein the high grade astrocytoma is brain stem glioma.

16. The method of claim 8 wherein the high grade astrocytoma is brain stem glioma.

* * * * *

UNITED STATES PATENT AND TRADEMARK OFFICE
CERTIFICATE OF CORRECTION

PATENT NO.   : 5,942,247
DATED        : August 24, 1999
INVENTOR(S)  : Margaret H. Dugan It is certified that error appears in the above-identified patent and that said Letters Patent is hereby corrected as shown below:

<u>Title page,</u>
Item [75], add -- Pascale Reidenberg -- as the second inventor.

Signed and Sealed this

Nineteenth Day of August, 2003

JAMES E. ROGAN
*Director of the United States Patent and Trademark Office*